United States Patent [19]

Bade

[11] 4,071,544
[45] Jan. 31, 1978

[54] PROCESS FOR THE MANUFACTURE OF CITRIC ACID ESTERS OF PARTIAL FATTY ACID GLYCERIDES

[75] Inventor: Volkbert Bade, Essen, Germany

[73] Assignee: Th. Goldschmidt AG, Essen, Germany

[21] Appl. No.: 633,718

[22] Filed: Nov. 20, 1975

[30] Foreign Application Priority Data

Nov. 27, 1974 Germany ............................. 2455989

[51] Int. Cl.² .................................................. C11C 3/02
[52] U.S. Cl. ..................................................... 260/410.7
[58] Field of Search ........................... 260/410.8, 410.7

[56] References Cited

U.S. PATENT DOCUMENTS

| | | | |
|---|---|---|---|
| 2,614,937 | 10/1952 | Baur et al. | 260/410.8 X |
| 2,813,032 | 11/1957 | Hall | 260/410.8 X |
| 2,938,027 | 9/1960 | Gladstone | 260/410.8 X |
| 3,227,559 | 1/1966 | Radlove | 260/410.8 X |

*Primary Examiner*—Winston A. Douglas
*Assistant Examiner*—John F. Niebling
*Attorney, Agent, or Firm*—Toren, McGeady and Stanger

[57] ABSTRACT

A method for making citric acid esters of fatty acid mono or diglycerides by reacting citric acid with the glycerides at elevated temperatures and in the presence of acetic acid as a solvent.

4 Claims, No Drawings

PROCESS FOR THE MANUFACTURE OF CITRIC ACID ESTERS OF PARTIAL FATTY ACID GLYCERIDES

BACKGROUND OF THE INVENTION

1. Field of the Invention

This invention relates to the production of citric acid esterified partial fatty acid glycerides.

2. Description of the Prior Art

The presently known esters of citric acid with partial fatty acid glycerides are used primarily in the food industry. Generally, they serve to stabilize fatty emulsions and to act as synergistic agents for antioxidants which are used in fatty or fat type products.

A number of methods are known for production of these esters. Thus, for example, in German Patent Auslegeschrift DT-AS 1,278,423, the manufacture of the esters is carried out by the direct reaction of the partial fatty acid glyceride with citric acid. However, this process has considerable disadvantages and relatively limited application.

Thus, for example, only one mol of citric acid can react with one mol of the fatty acid monoglyceride. If an attempt is made to increase the molar reaction of the citric acid, the participation of the citric acid is decreased and it precipitates as a product of the reaction. Moreover, if an attempt is made to force the reaction to completion by increasing the temperature, the citric acid is decomposed in an uncontrollable manner. Also, the hydrophilic properties of the reaction product are lowered and as a result of the formation of other by-products, the resulting mixture is often physiologically unsafe.

Another known process is the reaction of citric acid with acetic acid anhydride to form an acetyl compound and a citric acid anhydride and then to esterify the anhydride with a partial fatty acid ester. However, with this reaction, the pure citric acid ester of the partial monoglyceride is not obtained. Rather, products are obtained in which the hydroxyl group of the citric acid is acetylized.

Consequently, upon storage and use of these reaction products, the acetic acid splits off and detrimentally affects the smell and taste of the food to which the reaction products have been added.

SUMMARY OF THE INVENTION

Applicant has discovered a method for the production of citric acid esters of partial fatty acid glycerides which avoid the above noted disadvantages and which produces a product having the desired hydrophilic properties and which is also safe for consumption. Additionally, the amount of material which can be reacted is not as limited as in the prior art processes.

Particularly, applicant has discovered that when citric acid and a fatty acid mono- and/or diglyceride are reacted at elevated temperatures and wherein acetic acid is used as the solvent and sufficient acetic acid is present during the reaction to maintain a clear solution without any precipitate during the reaction, upon removal of the acetic acid, excellent yields can be obtained.

DESCRIPTION OF THE PREFERRED EMBODIMENT

More particularly, when acetic acid is used as a solvent for the reaction mixture, since the reaction products during the reaction are, in of themselves, solvents for the other reacting substances, it is possible to gradually remove the acetic acid during the reaction. Such removal may be accomplished in the conventional manner, as by distillation or evaporation. However, it is important that the removal of the acetic acid occur at a rate so as not to produce any precipitate of the insoluble products. Thus, the rate of removal of the acetic acid must be appropriate to maintain a clear reaction solution or mixture.

As the acetic acid is removed from the reaction, it is possible to slowly increase the temperature of the reaction during the course thereof.

The reaction also produces water, during the esterification and this water is preferably removed from the system by distillation. This can be conveniently accomplished by distilling the water from the reaction together with the acetic acid so long as the appropriate rate of removal of acetic acid is maintained in accordance with the conditions indicated hereinabove.

The esterification reaction is generally carried out within a temperature range from about 100° to 140° C where the reaction temperature is essentially determined by the boiling temperature of the acetic acid. As the reaction progresses and the content of acetic acid in the reaction mixture is decreased, the reaction temperature may be increased.

The reason for the above-noted temperature range is that at temperatures below about 100° C, the reaction velocity or rate decreases to such an extent as to make the reaction economically unfeasible and undesirable.

At temperatures above about 140° C, side reactions begin to occur or the citric acid begins to decompose. Consequently, it is undesirable to go above this limit from the point of view of obtaining a pure product.

Suitable partial fatty acid glycerides for use in the present invention include those of stearic acid, palmitic acid, myristic acid, lauric acid, capric acid, arachidic acid, behenic acid, and the like which are conventionally reacted with citric acid.

The relative amounts of citric acid to partial fatty acid glycerides in the reaction mixture can vary depending on the properties of the product desired. Preferably, however, the ratios are chosen so that about 0.16 to 0.10 mols of citric acid is used for each hydroxyl group on the partial glyceride. The citric acid esters thus obtained will exhibit hydrophilic and hydrophobic properties depending on the increasing esterification of the bound citric acid.

In this regard, the term HLB-value is utilized herein to define the hydrophilic properties. Specifically, the HLB-value is the balance of the hydrophilic and the hydrophobic properties of the esters. The lower the HLB-value, the more hydrophobic is the citric acid ester. Correspondingly, the higher the HLB-value, the more hydrophilic is the ester.

The concept of the HLB-value is defined in detail in the article by W. C. Griffin entitled "Classification of Surface-active Agents by HLB" in J. Soc. Cosmetic Chemists 1, 311 (1950) incorporated herein by reference.

If less than about 0.16 mols of citric acid per mol of hydroxyl group on the partial glyceride is used, the hydrophilic properties of the ester products are lowered. Even so, reaction products can be obtained at a mol ratio of less than about 0.5 mols of citric acid per mol of hydroxyl group on the fatty acid monoglycerides according to the present process and such products will be free of the degrading by-products and can be obtained at a higher output rate than heretofore obtainable. Consequently, even these materials will possess a considerably higher hydrophilic purity and, therefore, can be used in the food industry.

The citric acid esters produced by the present invention are usable in a wide variety of applications due to the many variations with respect to product properties which can be produced utilizing the present process.

Thus, if the fatty acid mono- or diglyceride is esterified with a relatively small amount of citric acid, for example, from about 0.1 to 0.25 mols of citric acid per hydroxyl group, one obtains a relatively hydrophobic emulsifier which will have a low HLB value of less than or equal to about 6. Such materials are particularly suitable for the manufacture of water and oil emulsions.

These emulsifiers are equally usable in the food industry as well as in the cosmetic industry. In the food industry, the hydrophobic products are used as anti-spray or splatter means in the manufacture of margarines or baking fats.

In the cosmetic industry, appropriate creams or other ointment-like preparations can be manufactured.

Esterified products which contain high molar proportions of citric acid possess an HLB value of generally above 8 which, oil and water emulsifiers due to the purity and physiological safety, can be used in the widest range with respect to the food industry, the cosmetic industry or the pharmaceutical industry.

If the amount of the citric acid which is bound by esterification is further increased, for example, to about 1 mol of citric acid per available hydroxyl group with a partial glyceride, one obtains products having an HLB value of greater than or equal to 12. Such products can be used in food industry, for example, as an auxiliary baking means, and in the cosmetic and pharmaceutical industry as a solution agent.

Esterified products having a high amount of the esterified citric acid represents substances which are easy to disperse or distribute in water and are acid and surface active. The properties of these materials correspond to materials used for wetting or cleansing purposes. Thus, they lend themselves for use in the manufacture of products, such as, hair shampoos.

An additional increase in the hydrophilic properties can be obtained by neutralizing the esterified products either wholly or partially with bases. Typically, alkalihydroxides would be suitable for use as the base.

These products are water soluble and possess high surface activity. It is further possible to disperse the products in water and to transform them by the addition of basic reacting salts, such as, sodium citrate into a clear water-soluble form.

One can further mix the reaction products in a dry state with basic reacting substances, such as, sodium citrate, sodium acetate, or sodium tartrate, such that the neutralization is then immediately effected merely upon the addition of water.

As a result of the present invention, it is thus possible to obtain pure and physiologically safe citric acid esters from fatty acid mono- and/or diglycerides in a relatively simple manner. It is further possible to simultaneously obtain products having hydrophilic properties over a wide range of HLB systems by choice of the ratio of the reaction components.

The following examples illustrate the present invention:

EXAMPLE 1

1,000 grams of glycerine mono fatty acid ester wherein the fatty acid components of stearic acid and palmitic acid are present in a mol ratio of 65 : 35, respectively, and 960 grams of citric acid (a molar ratio of approximately 1 : 2) were dissolved in 1000 grams of acetic acid and the mixture was heated to 130° C. Thereafter, the acetic acid was slowly distilled off during a period of 2 hours at a temperature of 130° C starting at normal pressure and then slightly decreasing the pressure to 10 Torr during the aforesaid period such that no precipitation occurred in the reaction mixture. The entire distillation time was about two hours. Thereafter, the reaction mixture, which was free of citric acid, was heated at this temperature for an additional three hours under vacuum.

The product obtained was brittle, wax-like, and had a slightly yellowish color. The acid number was 260 and the yield was 92%. An approximately 5% aqueous emulsion of the product possessed a gel-like character and the HLB value was about 12.

EXAMPLE 2

1,000 grams of glycerin mono fatty acid ester wherein the fatty acid components were stearic acid and palmitic acid in a molar ratio of 65 : 35, respectively, and 480 grams of citric acid (molar ratio of approximately 1 : 1) were dissolved in 1,000 grams of acetic acid and the mixture was allowed to react in the same manner as in Example 1.

A brittle, wax-like, slightly yellow reaction product was obtained having an acid number of 160 in a yield of 94%. A 15% aqueous emulsion exhibited weak gelling characteristics with certain portions being precipitated. The HLB value of the product was about 9.

EXAMPLE 3

300 grams of glycerin monolaurate and 384 grams of citric acid were dissolved in 360 grams of acetic acid and the mixture was allowed to react as in Example 1.

A highly viscose, slightly yellow reaction product having an acid number of approximately 310 was obtained. A 5% aqueous emulsion exhibited a transparent to clear dispersion and a low viscosity.

Having thus described my invention, what is claimed is:

1. In a method for the manufacture of citric acid esters from the esterification reaction of fatty acid monoglycerides and fatty acid diglycerides with citric acid at elevated temperature, the improvement which comprises carrying out the reaction in acetic acid as a solvent and removing the acetic acid during the reaction by distillation at a rate sufficient to maintain a clear reaction solution with no precipitate therein.

2. The method of claim 1 wherein the from about 0.16 to 1.0 mols of citric acid are used for each hydroxyl group of the glyceride.

3. The method of claim 1 wherein the esterification reaction is carried out in a temperature from about 100° to 140° C.

4. The method of claim 1 wherein the water produced from the esterification reaction is removed from the system by distillation along with the acetic acid.

* * * * *